(12) United States Patent
Friedman et al.

(10) Patent No.: US 10,070,805 B1
(45) Date of Patent: Sep. 11, 2018

(54) PATIENT MONITORING SYSTEM AND METHOD HAVING LOCATION-SPECIFIC CONTEXTUAL ALARMING

(71) Applicant: General Electric Company, Schenectady, NY (US)

(72) Inventors: Bruce Friedman, Jasper, GA (US); Matthew Grubis, New Berlin, WI (US); Scott Fuller, Greendale, WI (US); Eliana Stein, Madison, WI (US); Magnus Kall, Espoo (FI); Stephen Treacy, Milwaukee, WI (US); Peter Arndt, Germantown, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 15/456,893

(22) Filed: Mar. 13, 2017

(51) Int. Cl.
*A61B 5/11* (2006.01)
*G08B 21/04* (2006.01)
(Continued)

(52) U.S. Cl.
CPC ............ *A61B 5/1113* (2013.01); *A61B 5/002* (2013.01); *A61B 5/1118* (2013.01);
(Continued)

(58) Field of Classification Search
CPC ... A61B 5/1113; A61B 5/7405; A61B 5/1118; A61B 5/002; A61B 5/746;
(Continued)

(56) References Cited

U.S. PATENT DOCUMENTS 6,434,258 B2  8/2002  Wiens
8,018,584 B1  9/2011  Amir
(Continued)

FOREIGN PATENT DOCUMENTS

WO    03082094 A1   10/2003
WO   2016099521 A1   6/2016

OTHER PUBLICATIONS

Gorges, Mattias et al., "Improving Alarm Performance in the Medical Intensive Care Unit Using Delays and Clinical Context", International Anesthesia Research Society, vol. 108, No. 5, May 2009.
(Continued)

*Primary Examiner* — Brian Wilson
(74) *Attorney, Agent, or Firm* — Andrus Intellectual Property Law, LLP (57) ABSTRACT

A patient monitoring system includes a sensing device configured to measure physiological parameter data from a patient, an identification transmitter that transmits an identification signal, wherein the identification signal is associated with the patient, and a location tracking system having a plurality of identification receivers arranged in a care facility that receive the identification signal from the identification transmitter and determine a patient location within the care facility based on a location of receipt of the identification signal. The patient monitoring system further includes a contextual alarming module that receives the patient location and selects at least one location-specific alarm rule based on the patient location in the care facility. Physiological parameter data is then assessed by the patient monitoring system based on the location-specific alarm rule.

20 Claims, 6 Drawing Sheets

(51) Int. Cl.
  *G06F 19/00* (2018.01)
  *A61B 5/00* (2006.01)
(52) U.S. Cl.
  CPC ............ *A61B 5/7405* (2013.01); *A61B 5/746* (2013.01); *G06F 19/3418* (2013.01); *A61B 2562/08* (2013.01)
(58) Field of Classification Search
  CPC . A61B 2562/08; A61B 5/0002; A61B 5/0022; A61B 5/021; A61B 5/0472; A61B 5/1116; A61B 5/6802; A61B 5/14551; G06F 19/3418; G08B 21/0453
  See application file for complete search history.

(56) References Cited

U.S. PATENT DOCUMENTS

| | | | |
|---|---|---|---|
| 8,139,945 B1 | 3/2012 | Amir et al. | |
| 8,310,364 B2 | 11/2012 | Derks et al. | |
| 8,514,071 B2 | 8/2013 | Derks et al. | |
| 8,620,682 B2 | 12/2013 | Bechtel et al. | |
| 8,633,806 B2 | 1/2014 | Amir | |
| 9,055,928 B2 | 6/2015 | McCombie et al. | |
| 9,219,984 B1 | 12/2015 | Amir | |
| 9,306,665 B1 | 4/2016 | Amir | |
| 9,341,700 B2 | 5/2016 | Amir et al. | |
| 2008/0055074 A1 | 3/2008 | Gao et al. | |
| 2009/0275844 A1* | 11/2009 | Al-Ali | A61B 5/02438 600/500 |
| 2011/0001605 A1* | 1/2011 | Kiani | G06F 19/327 340/5.6 |
| 2011/0148624 A1* | 6/2011 | Eaton | H04W 4/028 340/539.13 |
| 2014/0077956 A1* | 3/2014 | Sampath | A61B 5/0022 340/573.1 |
| 2014/0145848 A1 | 5/2014 | Amir | |
| 2014/0266686 A1 | 9/2014 | Torgersrud et al. | |
| 2016/0228067 A1 | 8/2016 | Kuppuraj | |

OTHER PUBLICATIONS

International Search Report and Written Opinion for PCT Application PCT/US2018/022109, dated Jul. 4, 2018.

* cited by examiner

PATIENT MONITORING SYSTEM AND METHOD HAVING LOCATION-SPECIFIC CONTEXTUAL ALARMING

BACKGROUND

The present disclosure relates generally to medical devices and, more specifically, to medical monitoring devices for monitoring a patient's physiology and health status, especially wireless monitoring devices and systems.

In the field of medicine physicians often desire to continuously monitor multiple physiological characteristics of their patients. Oftentimes, such monitoring of multiple physiological characteristics involves the use of several separate monitoring devices simultaneously, such as a pulse oximeter, a blood pressure monitor, a heart monitor, a temperature monitor, etc. Many standard patient monitoring devices are large and bulky, tethering the patient to bedside devices via physical wiring or cabling that inhibits patient movement and requires a patient to stay in one location or transport a large monitor with them when they move from one place to another, and this discourages, rather than encourages, patient movement. Thus, continuous monitoring has the potential to conflict with treatment and recovery goals involving patient mobility, where patient activity is encouraged and requiring a patient to be active is recommended for expediting patient recovery. However, wireless monitoring devices have been developed that are relatively small devices that can be fixed to the patient, such as wearable devices. Such wireless monitoring devices allow patients to move around more freely, thus enabling continuous monitoring of multiple physiological characteristics without inhibiting patient movement and discouraging speedy recovery.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

One embodiment of a patient monitoring system includes a sensing device configured to measure physiological parameter data from a patient, an identification transmitter that transmits an identification signal, wherein the identification signal is associated with the patient, and a location tracking system having a plurality of identification receivers arranged in a care facility that receive the identification signal from the identification transmitter and determine a patient location within the care facility based on a location of receipt of the identification signal. The patient monitoring system further includes a contextual alarming module that receives the patient location and selects at least one location-specific alarm rule based on the patient location in the care facility. Physiological parameter data is then assessed by the patient monitoring system based on the location-specific alarm rule.

One embodiment of a method of monitoring a patient includes transmitting an identification signal associated with the patient from an identification transmitter and receiving the identification signal at an identification receiver, wherein one of the identification receiver or the identification transmitter is at a known location. A patient location within a care facility is then determined based on the known location of the identification receiver or the identification transmitter. At least one location-specific alarm rule is selected based on the patient location. Physiologic parameter data is measured from the patient and assessed based on the location-specific alarm rule.

Various other features, objects, and advantages of the invention will be made apparent from the following description taken together with the drawings.

BRIEF DESCRIPTION OF THE DRAWINGS

The present disclosure is described with reference to the following Figures.

DETAILED DESCRIPTION

The present inventors have recognized that wireless monitoring systems are desirable for patient comfort, for example to provide more comfort and mobility to the patient being monitored. The patient's movement is not inhibited by wires between sensor devices and/or computing devices that collect and process the physiological data from the patient. Thus, small sensing devices and sensors that can be easily attached to the patient's body are desirable, such as sensing devices that are wearable portable computing devices. However, the inventors have recognized that wearable monitoring systems present certain new challenges due to the fact that patient movement is less inhibited and that monitoring devices need to adjust to the context of the patient, such as to adjust monitoring and alarming to account for the patient's current activity. Part of interpreting a patient's activity, and thus interpreting physiological data recorded from the patient, includes identifying conditions that are likely to present noise issues or false alarms. This requires accounting for the context surrounding the patient.

The inventors have recognized that a patient's location within a healthcare facility can be utilized to provide such contextual information. Understanding where a patient is within a healthcare facility can provide information regarding, for example, the type of treatment that the patient is likely to be undergoing. For instance, if a patient's location indicates that the patient is in a physical therapy ward of a care facility, such information can be utilized to provide context as to changes in the physiological data recorded from the patient, such as elevated heartrate and blood pressure, and increased noise in the physiological measurements. Accordingly, the system may be configured to expect such conditions—e.g., increased noise, an elevated heartrate, and increased blood pressure—and alarm thresholds can be adjusted accordingly. This location-based alarm assessment helps reduce false alarms, which can be disruptive to patient care and/or unnecessarily utilize resources. By reducing false alarms, location-based alarming also reduces alarm fatigue.

Similarly, the system may make certain adjustments to operation of the sensing devices based on the location, such as to avoid taking noise-sensitive physiological measurements in environments where a high degree of noise is likely to be present. For example, the system may be configured to avoid taking a non-invasive blood pressure measurement while the patient is in the physical therapy ward, since non-invasive blood pressure measurements require a patient to be sitting and still and such conditions are less likely to occur during physical therapy. As another example, the operation of the ECG sensing device may be adjusted to record a more limited set of cardiac information from the patient, focusing on robust measurements that can be more reliably measured in noisy situations.

Additionally, the inventors have recognized that the alarm generation modality and alarm generation location can be adjusted to account for a patient's location within a care facility, thereby providing better and more targeted alarm notifications that alert the proper clinicians more immediately and avoid unnecessary alarm notifications that contribute to alarm fatigue. For example, the system can determine based on the patient's location where to sound the alarm so that an appropriate clinician can be alerted, such as to sound an alarm at a nearest nurses' station and/or sound an alarm locally at the patient, such as via a hub device associated with the wireless monitoring system. In still other embodiments, the system may be configured to suppress an audio alarm modality when the patient is at certain locations and/or engaged in certain activities where visual alarms would be sufficient to alert a clinician and audio alarms would be disruptive.

Additionally, the inventors have recognized that equipping the monitoring system with an activity sensor, such as an accelerometer and/or a gyroscope can provide additional contextual information regarding the patient's activity at the determined location. The activity information, such as information regarding the patient's position and/or motion, can be used to supplement and fine tune the location-based alarm rules, such as by providing location-specific alarm parameters that account for the patient's activity at the particular location. For example, alarm limits may be increased and/or alarms may be suspended when the activity sensor indicates that the patient is upright and moving and the location tracking system indicates that the patient is at certain predefined locations other than the patient's room. Namely, if the patient is walking or otherwise engaged in coordinated physical activity, that patient is unlikely to be experiencing a clinically relevant alarm condition.

In various embodiments, a patient monitoring system 1 may include one or more wireless sensing devices (e.g. 3a-3c), each measuring different physiological parameter data from a patient. For example, the wireless sensing devices 3a-3c may be networked to a central hub or primary sensing device that determines a patient condition and regulates the various sensing devices in the network. In certain embodiments having a hub 15, the hub device may communicate with a central network for the medical care facility, e.g., host network 30. In another embodiment, the wireless sensing devices may communicate directly with the host network, which may coordinate and/or regulate the operation of the various sensing devices. There, the wireless sensing devices may communicate with the host network directly, or indirectly, through the hub. For example, the hub may serve as an amplifier and/or router for communication between the wireless sensing devices and the host network. In such embodiments, each sensing device may process its own physiological parameter data and determine its own alarming conditions or such functions may be performed at the level of the host network.

Figure 1:
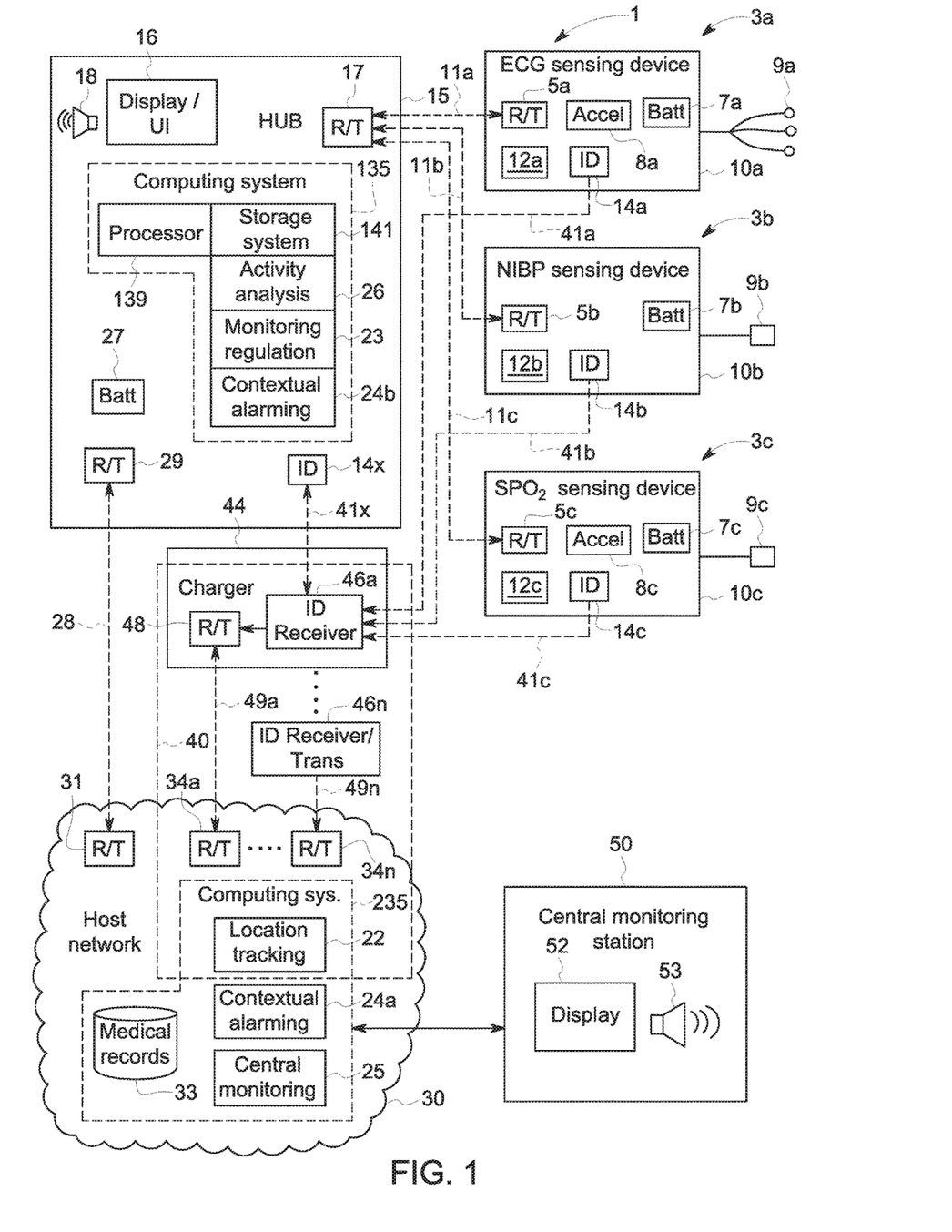
FIG. 1 provides a schematic diagram of an exemplary patient monitoring system according to the present disclosure.

FIG. 1 depicts one embodiment of a patient monitoring system 1 containing three wireless sensing devices 3a-3c in wireless communication with a hub 15. The hub 15 is in wireless communication with a host network 30 that contains medical records database 33. For example, the hub device 15 may be attached to the patient's body, placed on or near the patient's bed, or positioned within range of the patient, such as in the same room as the patient. The hub device 15 may be a separate standalone device, or it may be incorporated and/or housed with another device within the system 1, such as housed with one of the wireless sensing devices 3a-3c.

Each wireless sensing device 3a-3c contains one or more sensors 9a-9c for measuring physiological parameter data from a patient, and also includes a data acquisition device 10a-10c that receives the physiological parameter measurements from the sensors 9a-9c and transmits a parameter dataset based on those measurements to the hub device 15 via communication link 11a-11c. The sensors 9a-9c may be connected to the respective data acquisition device 10a-10c by wired or wireless means. The sensors 9a-9c may be any sensors, leads, or other devices available in the art for sensing or detecting physiological information from a patient, which may include but are not limited to electrodes, lead wires, or available physiological measurement devices such as pressure sensors, flow sensors, temperature sensors, blood pressure cuffs, pulse oximetry sensors, or the like. In the depicted embodiment, a first wireless sensing device 3a is an ECG sensing device having sensors 9a that are ECG electrodes. A second wireless sensing device 3b is a non-invasive blood pressure (NIBP) sensing device with a sensor 9b that is a blood pressure cuff including pressure sensors. A third wireless sensing device 3c is a peripheral oxygen saturation (SpO2) monitor having sensor 9c that is a pulse oximetry sensor, such as a standard pulse oximetry sensor configured for placement on a patient's fingertip. It should be understood that the patient monitoring system 1 of the present disclosure is not limited to the examples of sensing devices provided, but may be configured and employed to sense and monitor any physiological parameter of the patient. The examples provided herein are for the purposes of demonstrating the invention and should not be considered limiting.

The data acquisition device 10a-10c of each of the exemplary wireless sensing devices 3a-3c may include analog-to-digital (A/D) converters, which may be any devices or logic sets capable of digitizing analog physiological signals recorded by the associated sensors 9a-9c. For example, the A/D converters may be Analog Front End (AFE) devices. The data acquisition devices 10a-10c may further include processing units 12a-12c that receive the digital physiological data from the A/D converters and create physiological parameter data for transmission to the hub device 15 and/or to the host network 30. Each data acquisition device 10a-10c may be configured differently depending on the type of wireless sensing device, and may be configured to perform various signal processing functions and/or sensor control functions. To provide just a few examples, the processing unit 12a in the ECG sensing device 3a may be configured to filter the digital signal from the ECG sensors 9a to remove artifact and/or to perform various calculations and determinations based on the recorded cardiac data, such as heart rate, QRS interval, ST-T interval, or the like. The processing unit 12b in the NIBP monitor 3b may be configured, for example, to process the physiological data recorded by the sensors 9b in a blood pressure cuff to calculate systolic, diastolic, and mean blood pressure values for the patient. The processing unit 12c of the SpO2 sensing device 3c may be configured to determine a blood oxygenation value for the patient based on the digitized signal received from the pulse oximetry sensor 9c.

Accordingly, the processing unit 12a-12c may develop physiologic parameter data that, in addition to the recorded physiological data, also includes values measured and/or calculated from the recorded physiological data. The respective processing units 12a-12c may then control a receiver/transmitter 5a-5c in the relevant wireless sensing device 3a-3c to transmit the physiologic parameter data to the hub device 15 via communication link 11a-11c. The physiologic parameter data transmitted from the respective wireless sensing devices 3a-3c may include the raw digitized physiological data, filtered digitized physiological data, and/or processed data indicating information about the respective physiological parameter measured from the patient. Additionally, one or more of the data acquisition devices 10a-10c may be configured to compare the physiologic parameter data to one or more alarm thresholds to determine the presence of an alarm condition. In certain embodiments, the alarm thresholds may be determined by the contextual alarming module 24 executing steps described herein to set on or more location-specific alarm rules containing alarm thresholds. In such an embodiment, the location-specific alarm rules may be received at the respective sensing device 3a-3c via transmission by the hub 15 or the host network 30, which are determined by the methods and systems described herein.

In other embodiments, the processing units 12a-12c may not perform any signal processing tasks and may simply be configured to perform necessary control functions for the respective wireless sensing device 3a-3c. In such an embodiment, the parameter data set transmitted by the respective processing unit 12a-12c may simply be the digitized raw data or digitized filter data from the various sensor devices 9a-9c.

The receiver/transmitter 5a-5c of each wireless sensing device 3a-3c communicates via the respective communication link 11a-11c with the receiver/transmitter 17 of the hub device 15, which may include separate receiving and transmitting devices or may include an integrated device providing both functions, such as a transceiver. The receiver/transmitters 5a-5c of the wireless sensing devices 3a-3c and the receiver/transmitter 17 of the hub device 15 may be any radio frequency devices known in the art for wirelessly transmitting data between two points. In one embodiment, the receiver/transmitters 5a-5c and 17 may be body area network (BAN) devices, such as medical body area network (MBAN) devices, that operate as a wireless network. For example, the wireless sensing devices 3a-3c may be wearable or portable computing devices in communication with a hub device 15 positioned in proximity of the patient. Other examples of radio protocols that could be used for this purpose include, but are not limited to, Bluetooth, Bluetooth Low Energy (BLE), ANT, and ZigBee.

In various embodiments, one or all of the sensing devices 3a-3c may be equipped with an identification transmitter 14a-14c that emits an identification signal that is detected by a location tracking system 40. The location tracking system 40 receives the identification signal in order to determine the patient's location. The tracking system 40 may be, for example, a real-time location system (RTLS) that provides immediate or real time tracking of the patient's location. In the embodiment of FIG. 1, each sensing device 3a-3c includes an identification transmitter 14a-14c that transmits an identification signal associated with the patient. Since the sensing devices 3a-3c are body-worn devices, the identification signal can be used to determine a patient location within the care facility. A plurality of identification receivers 46a-46n are placed at known locations throughout a care facility. The identification signal transmitted by the identification transmitter 14a-14c is thus received by one of the identification receivers 46a-46n closest to, or otherwise arranged to receive transmissions from, identification transmitters at that particular location of the patient. Each identification receiver 46a-46n then communicates the identification signal, along with its own receiver identification, to a location tracking module 22 that monitors and determines the patient location for the location tracking system 40 within the care facility. For example, the identification receiver 46a, 46n may communicate the identification signal and its own identification with a host network 30 for the care facility.

The location tracking module 22 then determines a patient location based on which identification receiver 46a-46n receives the identification signal for that patient from one or more of the identification transmitters 14a-14c. Specifically, the location tracking module 22 accesses a map or database of the care facility where each identification receiver 46a-46n is associated with a particular location in the care facility. The map associating each identification receiver 46a-46n with a physical location in the care facility may be, for example, uploaded and stored in the computing system 235 of the host network 30 as part of the system configuration.

In certain embodiments, the sensing devices 3a-3c my coordinate their transmission of the identification signal by the identification transmitters 14a-14c so that the transmissions are spaced out in time. Thereby, the identification signal can be transmitted more frequently and redundancy between the sensing devices 3a-3c can be reduced. Such coordination provides an efficient use of resources, including battery power, because it limits the frequency at which each sensing device transmits the identification signal. In other embodiments, the identification transmitters 14a-14c may independently and/or simultaneously transmit the identification signal, which may be used to provide redundancy and certainty to the patient location determination. In certain embodiments, the identification signal transmitted by the identification transmitters 14a-14c may be identical to one another, or may be different identification signals that are each associated with the patient.

The hub 15 may also include an identification transmitter 14x that transmits a location of the hub 15. Such identification transmitter 14x in the hub 15 may be in lieu of or in addition to the identification transmitters 14a-14c in the sensing devices. In embodiments where the hub 15 is a small, body-worn device that is attached to the patient, the identification transmitter 14x in the hub 15 may be sufficient for patient location tracking purposes. In embodiments where the hub 15 is not a body-worn device, the identification transmitter 14x may be unreliable, by itself, for patient location tracking. In such embodiments, the identification transmitter 14x may be used for tracking the location of the hub 15 separately from the patient.

Identification receivers 46 may be provided at fixed locations throughout the care facility, such as at each room, bed, bay, hallway, etc. to enable tracking the patient's location throughout the care facility. Each patient and their associated wireless monitoring system may be assigned a primary identification receiver 46. For example, the primary identification receiver (e.g., 46a) may be located at the location where the patient is likely to spend the most time, such as the patient's assigned room, bed, bay, etc. For example, each patient room may be equipped with an identification receiver 46 dedicated to that room, which may then be associated to the patient when the patient 4 is assigned to that room. Any identification signal received by the primary identification receiver 46a is assumed to indicate that the patient is located in their assigned room.

In certain embodiments, a primary identification receiver (e.g., 46a for patient 54a) may be provided in a charger 44 associated with the monitoring system, such as associated with one or more of the sensing devices 3a-3c. As the charger 44 is a device that must remained plugged in to a power source, such as a wall outlet, the charger 44 is not a portable device and thus remains at a relative fixed location during a monitoring period. For example, the charger 44 may remain plugged in to a wall outlet in a patient's room, or otherwise remain plugged into a particular power source. Thus the charger 44 remains at a relative fixed and known location—e.g., movement of the charger 44 is restricted by the length of the power cord connecting it to the power source. Accordingly, the charger 44 provides a reliable fixed and known location for placement of the identification receiver in a patient's room.

For example, each sensing device 3a-3c may have a battery 7a-7c that is charged by the respective charger 44. The battery 7a-7c may be a removable battery that can be removed from the respective sensing device 3a-3c and placed on the charger 44 for charging, and a replacement battery may be inserted into the respective sensing device 3a-3c. For example, all of the sensing devices 3a-3c may utilize identical batteries 7a-7c, and thus the charger 44 may provide a bank of charging slots where batteries can be swapped and charged as each sensing device requires. Alternatively, the charger 44 may be configured to connect to each respective sensing device 3a-3c in order to charge the respective batteries 7a-7c. Likewise, the charger 44 may be configured to charge a battery 27 of the hub 15.

The identification transmitters 14a-14c, 14x communicate with one of a plurality of identification receivers 46a, 46n via a respective communication link 41a-41c, 41x. The communication link 41a-41c, 41x may be by any of various wireless communication protocols and/or platforms, such as Bluetooth, Bluetooth Low Energy (BLE), ZigBee, Wi-Fi, infrared, ultrasound, or by other wireless communication means. In certain embodiments, it is preferable that the transmission range of the identification signal be limited so that the identification transmitters 14a-14c, 14x are only within communication range of one identification receiver 46a-46n at a time. Thus, it may also be beneficial if the system is configured such that the communication signals and protocols do not pass through walls or other structural barriers so that identification receivers 46a, 46n can be placed in adjacent rooms, such as adjacent hospital rooms, without concern of cross-receiving. Accordingly, infrared may provide a good means for the communication links 41a-41c, 41x in other embodiments where line-of-sight limitations are prohibitive, other relatively short-range protocols may be desirable, such as Bluetooth, Bluetooth Low Energy (BLE), or ZigBee, or the like.

The identification receiver 46a, 46n may communicate with the host network via a separate receiver/transmitter that communicates with a respective receiver/transmitter 34 associated with the host network 30. Alternatively, one or more of the identification receivers 46a-46n may have a transmitter incorporated therein capable of transmitting the identification signal and its own receiver identifier to a respective receiver/transmitter 34n associated with the host network 30. The identification signal is communicated to the host network 30 via a respective communication link 49a-49n, which may be by any wireless or wired means and according to any communication protocol. For example, communication may be via a Wi-Fi network for the care facility, or by a dedicated wireless network for the location tracking system 40. For example, in certain embodiments the location tracking system 40 may employ one or more wireless local area networks (WLANs) situated throughout a care facility. In other embodiments, the devices on the location tracking system 40 may utilize the (WMTS) spectrum.

In certain embodiments, the identification transmitter 14a-14c, 14x may be incorporated into the receiver/transmitter 5a-5c, 17 associated with the respective sensing device 3a-3c and/or hub 15. In such an embodiment, the identification signal may be transmitted by the respective receiver/transmitter 5a-5c, 17, such as on the same network as the physiologic parameter data. For example, in an embodiment where the sensing devices 3a-3c communicate directly to a host network 30, the identification signal may be transmitted in conjunction with the physiological parameter data, which are received at a receiver associated with the host network 30, wherein the receiver is at a known location in the care facility.

In the embodiment depicted in FIG. 1, the identification transmitters are provided in the sensing devices 3a-3c and/or the hub 15 with the identification receivers 46a-46n provided at fixed and known locations throughout the care facility. In other embodiments, the identification receivers 46a-46n may travel with the patient, such as provided in the sensing devices 3a-3c and/or the hub 15 (and the identification transmitters 14 may be provided at fixed locations throughout the care facility). In such an embodiment, the respective sensing devices 3a-3c or hub 15 would receive the identification signal from a nearby identification transmitter 14 and may be equipped to determine its own location based on the identification signal received.

The location tracking module 22 is configured to receive the identification signal associated with the patient as well as the identification of the receiver 46a, 46n that received that identification signal for the patient. Based thereon, the location tracking module 22 determines a patient location within a care facility. For example, the location tracking module 22 may be configured with a map of a care facility, where a location of each identification receiver 46a-46n is associated to a location on the map. Thus, when an identification signal is received at a particular identification receiver 46a, 46n, the location tracking module 22 determines the patient location for the patient associated with the identification signal to be a given location range on the map of the care facility associated with the identification receiver 46a, 46n that received the identification signal. For example, the patient location may be determined to be the patient room associated with the identification receiver 46a assigned to or associated with that room.

As a patient moves throughout a care facility, the identification signal transmitted by the identification transmitters 14a-14c, 14x associated with the patient are received by different identification receivers 46a, 46n, and the location tracking module 22 may update the patient's location as a new identification receiver 46a, 46n reports receiving the identification signal. Additionally, the location tracking module 22 may store the patient location in order to track and store the patient's location over time. For example, a location pattern may be stored and generated for a patient's stay at a particular care facility.

The hub device may further include computing system 135 having processor 139 and storage system 141. The hub device 15 may serve to control the wireless sensing devices 3a-3c, and thus may transmit operation commands to the respective wireless sensing devices 3a-3c via the communication link 11a-11c to control their monitoring operations. The hub 15 may contain a monitoring regulation module 23 that is a set of software instructions stored in memory and executable on the processor to assess the physiologic parameter data collected by the wireless sensing devices 3a-3c and determine a patient condition therefrom, and to control the respective wireless sensing devices 3a-3c according to the patient condition. For example, the patient condition may be determined by comparing the physiologic parameter data collected by one or more of the sensing devices 3a-3c with alarm limits to determine whether the patient condition requires generating an alarm to alert the clinician to the patient's condition. In the embodiment of FIG. 1, the monitoring regulation module 23 is stored and executed within the hub 15; however, in other embodiments the monitoring regulation module 23 may be stored and executed within a host network 30, such as where the sensing devices 3a-3c communicate directly with the host network 30.

The hub device 15 may further include a display 16 and a speaker 18 that may be used to generate an alert or alarm. Specifically, if one or more alarm limits are met, the computing system 135 of the hub 15 may control the display 16 to generate a visual alarm indicator, and/or may control the speaker 18 to generate an auditory alarm indicator. The display 16 may be any type of digitally-controlled visual display, and may further be a touchscreen controllable by a user to provide input to the hub 15, such as to silence an alarm. The alarm may be generated by the display 16 and/or by the speaker 18 according to the location-specific alarm rule. Alternatively or additionally, the location-specific alarm rule may require alarm generation at a central monitoring station 50, such as may be provided at a nurses' station or other central location where clinicians can be alerted and can access alarm data. The central monitoring station 50 includes a display 52 and speaker 53, each of which may selectively be used to generate an alarm according to the location-specific alarm rule. For example, the alarm may be generated at the central monitoring station closest to the patient's location, which may be in addition to or in alternative to generating the alarm locally at the hub 15 or some other audio or visual alarm generator at the patient's location.

In the system of FIG. 1, a contextual alarming module 24 receives the patient location, such as from the location tracking module 22, and selects one or more location-specific alarm rules based on the patient location in the care facility. For example, location-specific alarm rules may include various parameters, requirements, and/or constraints relating to alarming. For instance, the location-specific alarm rules may include alarm limits for one or more physiological parameters being monitored by the sensing devices 3a-3c, such as threshold values or patterns for the physiologic parameter data that trigger alarm generation.

Alternatively or additionally, the location-specific alarm rules may include alarm modality instructions—i.e., specifying what means should be used to generate the alarm. Examples of alarm modalities include auditory alarms, such as generated by speakers, visual alarms, such as generated on digital displays or by lights that illuminate or blink to indicate a patient alarm, or by physical means, such as a vibrating device worn by a clinician, or any combination of the foregoing. The location-specific alarm rule may further include alarm generation location information specifying where in a care facility and/or by what devices an alarm should be generated. For example, an alarm generation location might be, or include, a central monitoring station closest to the current patient location for the alarming patient. Alternatively or additionally, the alarm generation location might instruct local alarming by monitoring devices associated with the patient, such as instructing alarming at the hub 15 and/or at a respective sensing device 3a-3c.

Alternatively or additionally, the location-specific alarm rules may dictate the type of information provided in the alarm notification. For example, when the patient is not at their primary location (e.g., in their room) the location-specific alarm rule(s) may require an alarm notification to include a patient location indicator indicating the patient location to the recipient of the alarm notification. For example, the location indicator may be a written description of the patient's location—for instance, "in Hall A, South Side, near Room X" or "in Imaging, Room Y". Alternatively, the location indicator may be a map or chart pictorially describing the patient location, such as providing a symbol in the floor plan of the care facility.

The location-specific alarm rules are determined based on the patient's location. For example, each location in a care facility may be associated with a predefined set of location-specific alarm rules. Similarly, each location in a care facility may be associated with several different location-specific alarm rules, and in any given situation the contextual alarming module 24 may select one or a subset of the location-specific alarm rules for a given patient location based on additional information, such as based on a patient's activity and/or based on patient-specific information, such as information available from the patient's medical record. For example, ECG alarm limits may be established differently for a cardiac patient at a given location than for a patient that is not being cared for a cardiac issue.

The contextual alarming module 24 is a set of software instructions executed on one or more processors within the patient monitoring system 1. In various embodiments, the contextual alarming module 24 may be stored and executed within a computing system 235 of the host network 30. Alternatively or additionally, the contextual alarming module 24 may be contained locally within the physiological monitoring system attached to or associated with the patient. For example, the contextual alarming module 24 may be stored in and executed by a computing system 135 within the hub 15 and/or in one or more of the sensing devices 3a-3c. Further, in certain embodiments, the contextual alarming module 24 may be provided in multiple devices within the system 1, such as to carry out various aspects or steps of the methods described herein. In the embodiment of FIG. 1, the contextual alarming module 24 is comprised of instructions stored in and executed by both the computing system 235 of the host network 30 and the computing system 135 of the hub 15. Specifically, contextual alarming module portion 24a is stored within the storage system of the computing system 235, and contextual alarming module portion 24b is stored within the storage system 141 of the computing system 135. Together, the contextual alarming module portions 24a, 24b execute instructions to select at least one location-specific alarm rule based on the patient location in the care facility, and may further select the location-specific alarm rule based on other considerations, such as patient activity and/or information from the patient's medical record. In other embodiments, the contextual alarming module 24 may be entirely contained in either the computing system 235 of the host network 30 or the computing system 135 of the hub 15.

Once the contextual alarming module 24 determines the location-specific alarm rule or rules, those rules are applied to assess the physiological parameter data recorded by the one or more sensing devices 3a-3c. For example, the location-specific alarm rule(s) may be applied by the monitoring regulation module 23 within the hub device 15 to determine whether an alarm condition is present and to generate an alarm according to the location-specific alarm rule(s). Once an alarm condition is detected, alarms are then generated according to the location-specific alarm rules, such as at the specified generation locations.

For example, in one embodiment the contextual alarming module 24a in the host network may receive the patient location from the tracking module 22 and determine the location-specific alarm rule, or a set of possible location-specific alarm rules. The one or more location-specific alarm rules may then be communicated to the hub 15 via the communication link 28 between receiver/transmitter 31 of the host network 30 and receiver/transmitter 29 of the hub 15. Such wireless communications may be conducted according to any of various wireless means, as is described above. In certain embodiments, the contextual alarming module 24a may instruct the host network 30 to publish the location-specific alarm rules, which may then be accessed by the hub 15 according to its own routine and timing. For example, communication of the location-specific alarm rules from the host network 30 to the hub 15 may be via a publish-subscribe messaging pattern, or model. In such an embodiment, the host network 30 publishes the location-specific alarm rules, and the hub 15 subscribes to the published "messages" containing the location-specific alarm rules. Accordingly, the host network 30 does not need to establish a direct communication link with the hub 15, and vice versa, and each can continue to operate normally regardless of the other. In certain embodiments, the contextual alarming module portion 24a may determine and publish a set of location-specific alarm rules based on the patient's location in the care facility, which are received by a contextual alarming module portion 24b in the hub 15. The contextual alarming module portion 24b in the hub 15 may then identify or select at least one or a set of location-specific alarm rules based on additional information to which it has access, such as the patient's current activity.

In the depicted embodiment, the hub 15 contains an activity analysis module 26 that receives information from one or more activity sensors 8 attached to the patient. With reference to the exemplary embodiment of FIG. 1, the ECG sensing device 3a and the SPO2 sensing device 3c each contain an activity sensor 8a, 8c that monitors a position and/or motion of the respective data acquisition unit 10a, 10c, which is attached at a location on the patient's body. In one exemplary embodiment, the activity sensor 8a-8c may include an accelerometer (such as a three-axis accelerometer), a gyroscope (such as a three-axis gyroscope), or a combination accelerometer/gyroscope sensor. In still other embodiments, the activity sensor(s) 8a-8c may be another type of inertial sensor, such as including a magnetometer and/or any other type of sensor capable of acting as an accelerometer and/or a gyroscope.

Figure 2A:
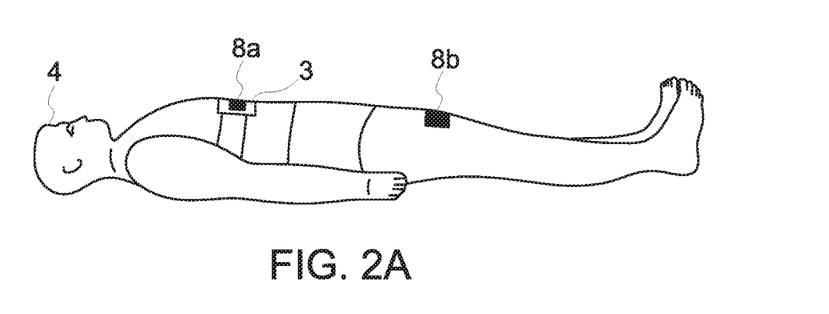
FIGS. 2A-2B depict embodiments of activity sensors connected to a patient as part of a patient monitoring system.
Figure 2B:
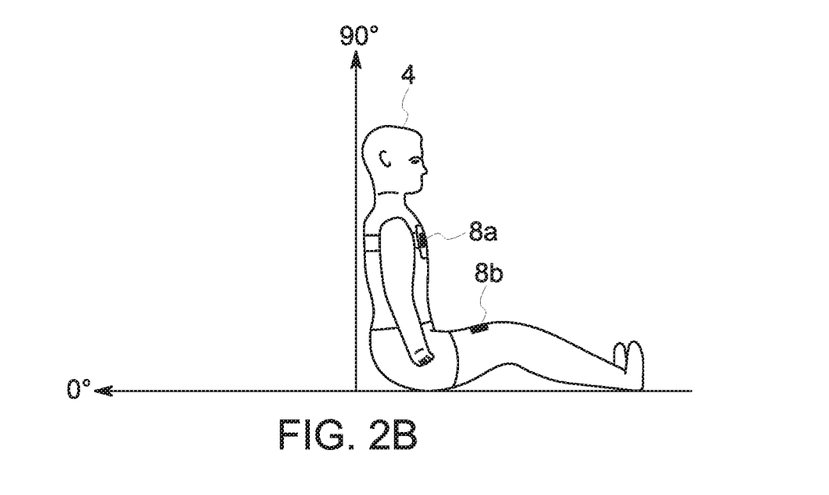

The activity sensors 8a-8c may be incorporated into the various sensing devices 3a-3c attached at various locations on the patient's body, or one or more activity sensors 8 may be stand alone devices attached at locations on the patient 4. FIGS. 2A and 2B illustrate an exemplary embodiment where one accelerometer 8a is incorporated into a sensing device 3 strapped to the patient's chest, which may be, for example, an ECG sensing device 3a. A second activity sensor 8b is attached to the patient's thigh. This can provide detailed position and motion information that may be used to detect the patient's position and motion. For example, the depicted arrangement of activity sensors 8a and 8b on the patient's torso and legs can be used to differentiate between a supine, seated upright, and standing position based on the orientation and/or direction of motion measured by the activity sensor 8. A position indicator 63 can then be generated accordingly. For instance, when the patient 4 is laying supine or in standing vertically both the activity sensors 8a and 8b will read the approximate orientation as one another—i.e., either both detecting horizontal orientation (i.e., indicating that the patient is lying horizontal) or both detecting vertical orientation (i.e., indicating that the patient is standing). However, when the patient is in the seated position as exemplified in FIG. 2B, the activity sensor 8a attached to the patient's chest will provide a vertical orientation and the activity sensor 8b attached to the patient's leg will provide a horizontal orientation.

Additionally, the depicted activity sensor 8a, 8b arrangement can also be arranged to sense information about the patient's motion, such as whether the patient is walking, and a motion indicator 65 can be generated accordingly. For example, the activity analysis module 26 may be configured to identify patterns of motion measured in one or more activity sensor and generate a corresponding motion indicator 65. For instance, the activity analysis module 26 may generate a "walking" motion indicator when the all of the activity sensors 8a-8c are measuring an approximate vertical orientation, and where significant orientation changes and patterns are detected in an activity sensor 8b on the patient's leg and/or an with lesser acceleration and/orientation changes measured by an activity sensor 8a on the patient's chest.

The activity information may be received by the activity analysis module 26 in the hub device 15, such as transmitted via the respective communication link 11a-11c between the sensing devices 3a-3c and the hub 15. The activity analysis module 26 determines at least one of a position indicator 63 and a motion indicator 65 (FIG. 3) based on the information received from the activity sensor 8a-8c. For example, the position indicator 63 may indicate one of a predetermined set of positions for the patient. To provide just one example, the activity analysis module 26 may select the position indicator 63 from a predefined list of positions, including supine, reclined, seated upright, standing upright, kneeling, bent forward, or the like. Alternatively or additionally, the activity analysis module 26 may determine a motion indicator 65 based on information from the activity sensors 8a-8c. The motion indicator 65 may be, for example, one of a predefined list of motion, including slow walking, fast walking, running, jumping, stair climbing, stationary with arm motion, stationary with leg motion, or the like.

The position indicator 63 and/or motion indicator 65 may then be used by the contextual alarming module 24 to further determine the location-specific alarm rules 70. For example, different location-specific alarm rules may be assigned to different position indicators 63 and/or motion indicators 65 at different locations in the care facility. For example, different alarm limits may be assigned and followed when the patient is in an upright seated position in their primary location, such as their hospital room, versus when the patient is in an upright seated position in the physical therapy section or ward of the care facility. Likewise, different location-specific alarm limits may be selected and implemented at a given location in the care facility based on the patient's position and/or motion. For example, a first alarm limit may be implemented when the position indicator 63 indicates that the patient is in the supine position and the motion indicator 65 indicates that the patient is still, and a different alarm limit may be implemented in that same location in the care facility when the patient is upright and moving.

In certain embodiments, the position and motion based portion of the alarm rules selection may be carried out by the contextual alarming module portion 24b at the hub 15. In other embodiments, the hub 15 may transmit the position indicator 63 and/or motion indicator 65 to the host network 30, and the contextual alarming module 24a therein may select the location-specific alarm rule based on both the patient location and the activity information according to the position indicator 63 and motion indicator 65.

The physiologic parameter data is then compared against the alarm limits set by the selected location-specific alarm rules in order to detect alarm conditions. For example, the alarm condition detection may be carried out by the monitoring regulation module 23, as is described above. In certain embodiments, the monitoring regulation module 23 may further control one or more of the sensing devices 3a-3c based on the detected patient location 68. For example, the monitoring regulation module 23 may instruct suspension of one or more measurement activities by the sensing devices 3a-3c at certain locations in a care facility, such as where significant noise is likely to be present or where wireless connectivity between the sensing devices 3a-3c and the hub 15 and/or the host network are likely to be poor. Further, the activity of the sensing devices 3a-3c may additionally be controlled based on the position indicator 63 and/or motion indicator 65, such as to account for the patient's likely activity based on the patient location and the measurements from the activity sensor(s) 8.

Figure 3:
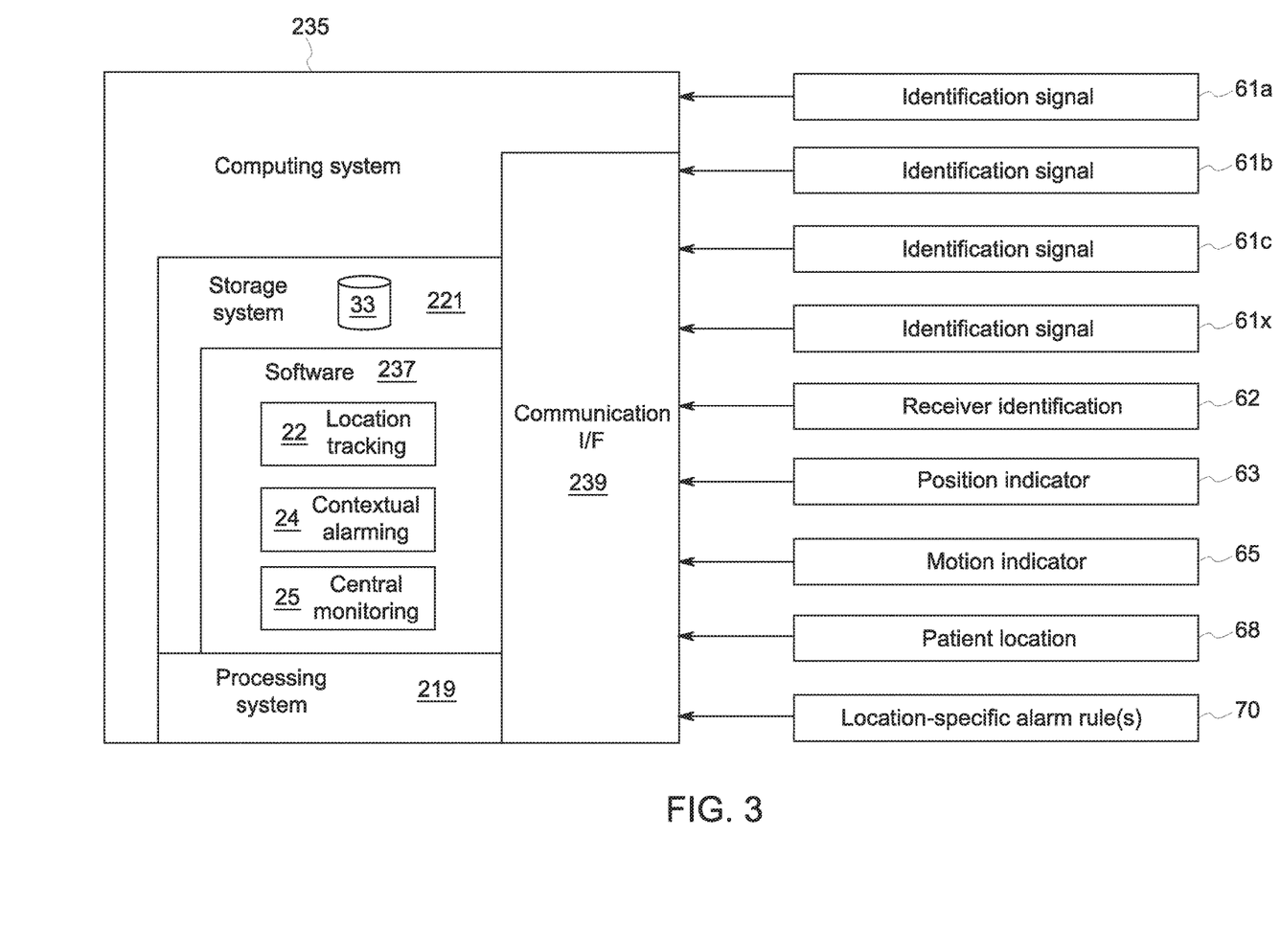
FIG. 3 is a schematic diagram of a computing system containing a contextual alarming module for a patient monitoring system.

FIG. 3 schematically depicts one embodiment of computing system 235 of the host network 30. The exemplary computing system 235 includes the contextual alarming module 24 for selecting one or more location-specific alarm rules, the location tracking module 22 for determining the patient location 68, and the central monitoring module 25 that cooperates with the monitoring regulation module 23 in the hub 15 to generate alarms for the patient 4 according to the location-specific alarm rule(s) 70, which each function variously as described herein. The computing system 235 generally includes a processing system 219, storage system 221, software 237, and communication interface 239. The processing system 219 loads and executes software 237 from the storage system 221, including the location tracking module 22, the contextual alarming module 24, and the central monitoring module 25, which are applications within the software 237. Each of the modules 22, 24, 25 include computer-readable instructions that, when executed by the computing system 235 (including the processing system 219), direct the processing system 219 to operate as described in herein in further detail, including to execute the steps to determine a patient location 68 and select location-specific alarm rules 70.

Although the computing system 235 as depicted in FIG. 3 includes one software 237 encapsulating one location tracking module 22, the contextual alarming module 24, and the central monitoring module 25, it should be understood that one or more software elements having one or more modules may provide the same operation. For example, the modules 22, 24, 25 may be combined into a shared set of instructions carrying out the steps described herein, or may be divided into any number of modules, which may be stored on separate storage devices and executed by different processing systems. Similarly, while description as provided herein refers to a computing system 235 and a processing system 219, it is to be recognized that implementations of such systems can be performed using one or more processors, which may be communicatively connected, and such implementations are considered to be within the scope of the description. For example, the computing system 235 may represent a cloud computing system and application implemented across multiple networked processing and storage devices.

The processing system 219 may include any one or more processing devices, such as one or more microprocessors, general purpose central processing units, application-specific processors, microcontrollers, or any other type of logic-based devices. The processing system 219 may also include circuitry that retrieves and executes software 237 from storage system 221. Processing system 219 can be implemented within a single processing device but can also be distributed across multiple processing devices or subsystems that cooperate in executing program instructions, such as in the cloud-computing application described above.

The storage system 221, which includes the patient medical record database 33, can comprise any storage media, or group of storage media, readable by processing system 219, and capable of storing software 237. The storage system 221 can include volatile and non-volatile, removable and non-removable media implemented in any method or technology for storage of information, such as computer-readable instructions, data structures, program modules, or other data. Storage system 221 can be implemented as a single storage device but may also be implemented across multiple storage devices or sub-systems. For example, the software 237 may be stored on a separate storage device than the medical record database 33. Likewise, medical record database 33 can be stored, distributed, and/or implemented across one or more storage media or group of storage medias. Similarly, medical record database 33 may encompass multiple different sub-databases at different storage locations and/or containing different information which may be stored in different formats. Storage system 221 can further include additional elements, such a controller capable of communicating with the processing system 219.

Examples of storage media include random access memory, read only memory, optical discs, flash memory, virtual memory, and non-virtual memory, magnetic sets, magnetic tape, magnetic disc storage or other magnetic storage devices, or any other medium which can be used to store the desired information and that may be accessed by an instruction execution system, as well as any combination or variation thereof, or any other type of storage medium. Likewise, the storage media may be housed locally with the processing system 219, or may be distributed in one or more servers, which may be at multiple locations and networked, such as in cloud computing applications and systems. In some implementations, the storage media can be a non-transitory storage media. In some implementations, at least a portion of the storage media may be transitory.

The communication interface 239 interfaces between the elements within the computing system 235 and external devices, such as various receiver/transmitters 31, 34a-34n that receive and transmit information to and from the host network 30. For example, the communication interface may operate to receive identification signals 61a-61c, 61x and the receiver identification 62 (providing the identification receiver 46a, 46n that received the identification signal(s)) generated via the location tracking system 40, receive position indicator(s) 63 and motion indicator(s) 65 from the hub 15 and/or directly from one or more of the sensing devices 3a-3c, and to transmit the patient location 68 and the location-specific alarm rule(s) 70.

Figure 4A:
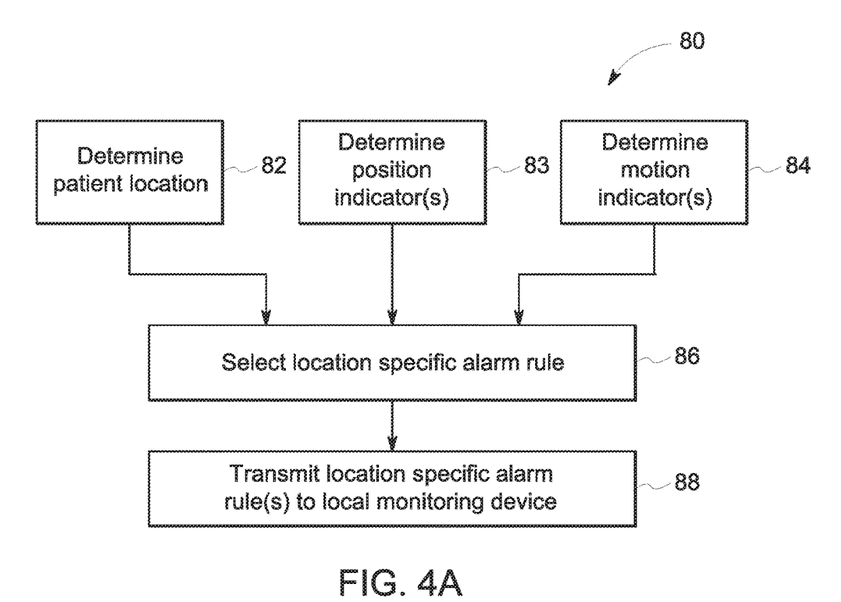
FIGS. 4A-4B and 5A-5B depict various aspects of exemplary methods of monitoring a patient.
Figure 4B:
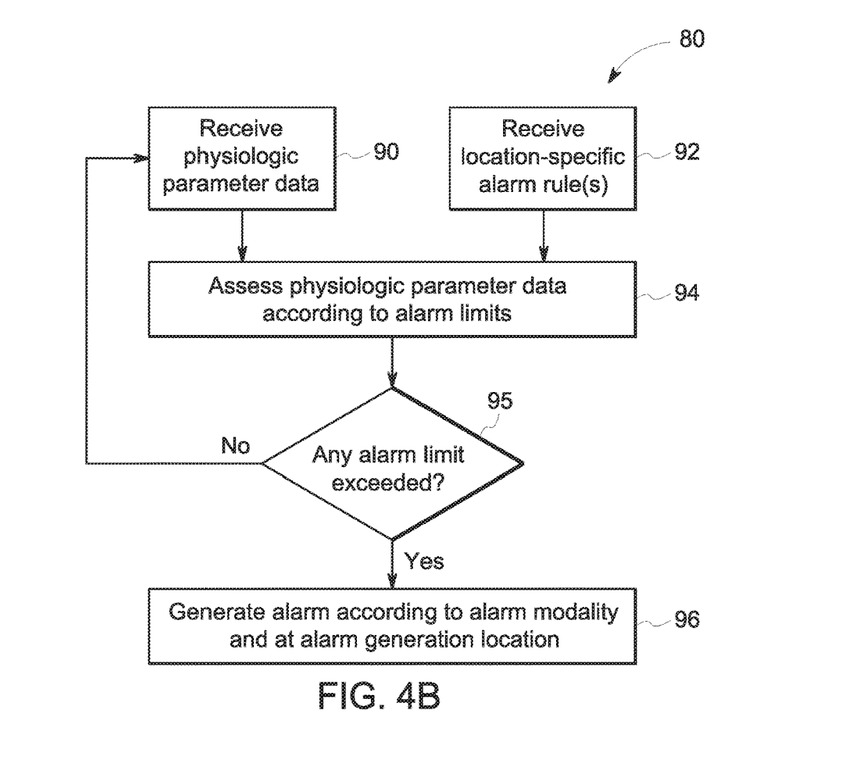
Figure 5A:
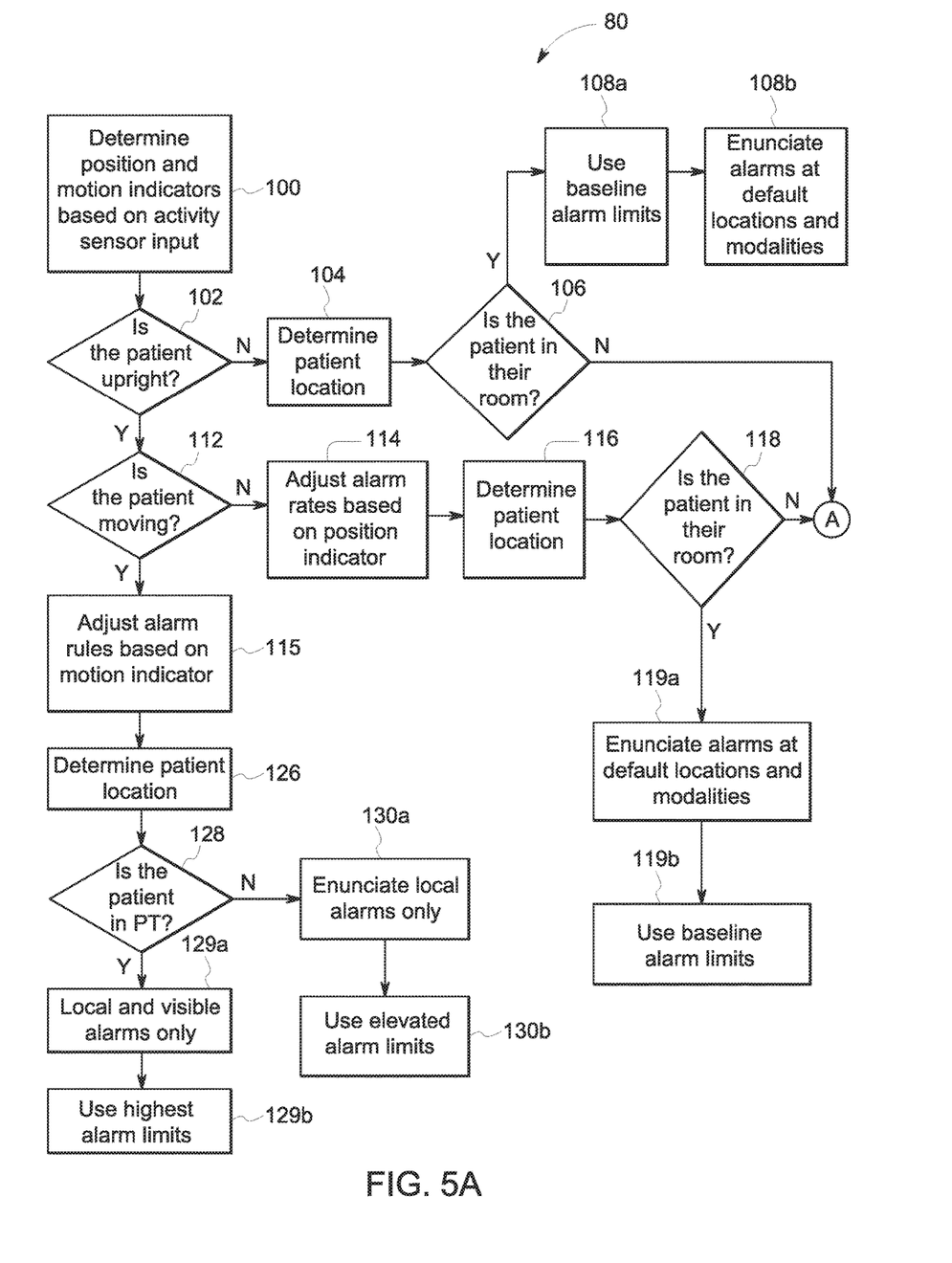
Figure 5B:
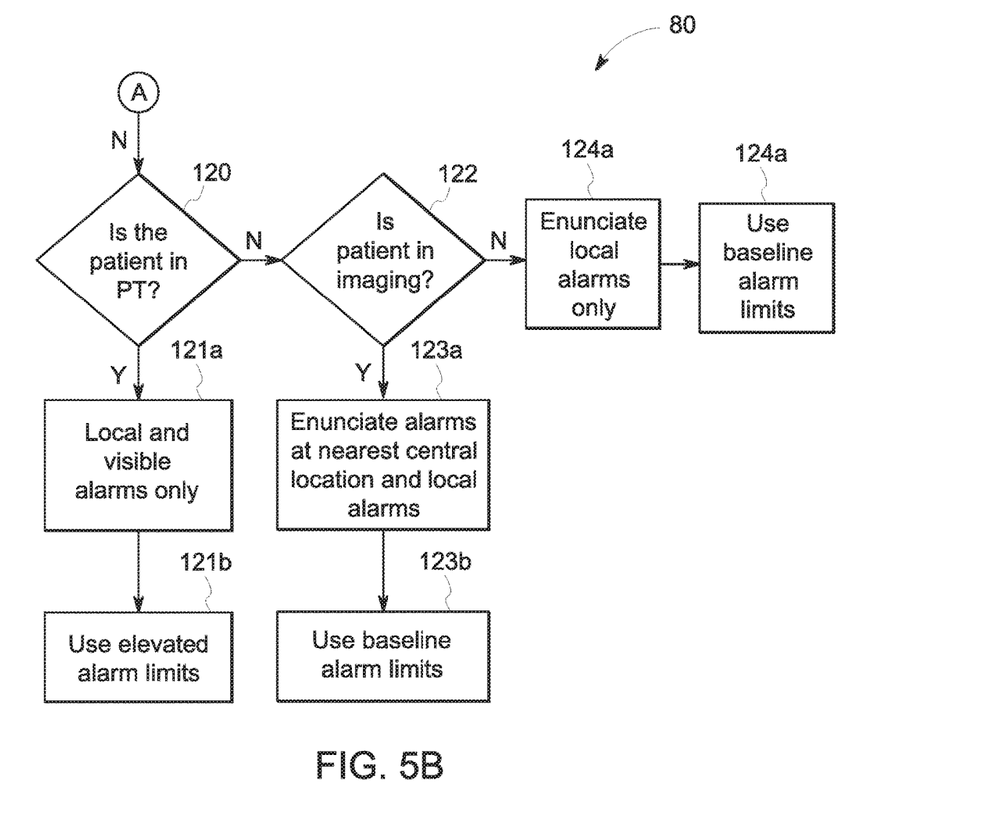

FIGS. 4A-4B and 5 depict various embodiments and aspects of a method 80 for monitoring a patient providing the location-specific alarming according to the present disclosure. In the example of FIG. 4A, a patient location is determined at step 82, such as by a location tracking module 22 executing the methods described above. A position indicator is determined at step 83 and a motion indicator is determined at step 84, such as by an activity analysis module 26 classifying the measurements from the activity sensors 8a-8c as described above. A location-specific alarm rule is selected at step 86 based on the patient location, position indicator, and motion indicator. The location-specific alarm rule is then transmitted at step 86 to the local monitoring device, such as to the hub 15 associated with the patient.

FIG. 4B depicts a subsequent portion of the method 80 for patient monitoring. Physiologic parameter data is received at step 90, such as from one or more sensing devices 3a-3c. Location-specific alarm rules are received at step 92, such as from a contextual alarming module 24 carried out by a host network 30 according to the steps depicted in FIG. 4A and also exemplified in FIG. 5. The physiologic parameter data is then assessed according to the location-specific alarm rules. Steps are executed at step 94 to assess the physiologic parameter data according to alarm limits specified by the location-specific alarm rules. If any alarm limit is exceeded at step 95, then step 96 is executed to generate an alarm according to the alarm modality and at an alarm generation location specified by the location-specific alarm rules. If no alarm limit is exceeded at step 95, then the system continues to assess the physiologic parameter data according to the most recent location-specific alarm rules received. In certain embodiments, the steps depicted in FIG. 4A may be executed by the host network 30, and the steps depicted in FIG. 4B may be executed at the hub 15. In other embodiments, the steps may be divided variously between computing systems 135 and 235, as is described herein.

FIG. 5 provides a further embodiment of a method 80 of patient monitoring, and specifically exemplifies steps executed to select a location-specific alarm rule. Position and motion indicators are determined at step 100 based on activity sensor input. Steps are executed at steps 102 to determine whether the patient position indicates that the patient is upright. If the patient is not in an upright position (such as lying supine or reclined), then steps are executed at step 104 to determine the patient location, such as by the location tracking system 1. Steps are executed at step 106 to determine whether the patient is at their primary location, such as at their assigned hospital room. If so, default alarm rules may be assigned. For example, baseline alarm limits may be assigned at step 108a and default alarm locations and modalities may be assigned at step 108b.

Returning to step 102, if the patient position is an upright position (such as sitting upright or standing), step 112 is executed to determine whether the patient is moving. In certain embodiments, additional logic could be executed if the patient is wheel-chair bound to detect when the patient is in a wheel chair versus sitting in their bed, for instance. If the patient is not moving, the alarm rules are adjusted at step 114 based on the patient position. If the patient is moving, then the alarm rules are adjusted at step 115 based on the motion indicator. For example, a predefined set of alarm rules may be selected at steps 114 and 115 based on the position and motion indicator respectively. That set of rules may then be further refined based on the patient location.

After step 114, the patient location is determined at step 116 and the location-specific alarm rules are identified based thereon. Steps are executed at steps 118 to determine whether the patient is in their room, which in this example is the primary location for the patient. If so, then the location-specific alarm rules are assigned at step 119, including assigning the default alarm generation locations and alarm modalities at step 119a and assigning the baseline alarm limits at step 119b. If the patient is not in their primary location, then further steps are executed to determine whether specific rules should be applied based on the patient's location. Step 120 is executed to determine whether the patient is in physical therapy. If so, then the location-specific alarm rules include requiring only local and visible alarms at step 121a and assigning elevated alarm limits at step 121b.

For example, local and visible alarms may be generated only locally to the patient, such as at the hub device 15 and/or at the sensing device 3a-3c recording the physiological parameter that triggered the alarm. The alarm may be shown, for example, on the display 16 associated with the hub 15, and would not be generated by the speaker 18. This would limit the intrusiveness of the alarm and avoid contributing to alarm fatigue given that the patient is undergoing physical therapy, one can expect that clinicians would be close by and attentive to the patient condition. Additionally, one can assume that the patient's activity is creating unreliability in the physiologic parameter data, and thus not providing reliable information regarding the patient's condition. Moreover, the patient's heart rate, blood pressure, etc. are likely to be elevated during physical therapy, and such conditions are expected and do not justify generation of an alarm.

If the patient is not in physical therapy, steps are executed at step 122 to determine whether the patient location indicates that the patient is undergoing imaging. If so, then the location-specific alarm rules include requiring that alarms be enunciated at the nearest central location, such as the nearest central monitoring station 50, as well as enunciating local alarms at step 123a, and assigning the baseline alarm limits at step 123b. If the patient location is not one of the special identified locations, such as physical therapy or imaging, then it may indicate that the patient is in transition from one care location to another. Accordingly, the location-specific alarm rules assigned may include enunciating local alarms only at step 124a and using baseline alarm limits at step 124b.

If the patient is determined to be moving at step 112, the alarm rules are adjusted based on the motion indicator at step 115. The patient location is determined at step 126 and then the rules are assigned based on the location. In the depicted example, steps are executed at step 128 to determine whether the patient is in physical therapy. If so, then location-specific alarm rules are assigned at step 129a requiring that alarms be generated locally and visibly only. The highest possible alarm limits may be set at step 129b. This is in consideration of the fact that the patient is moving and is engaged in physical therapy, which as described above creates unreliability in physiologic monitoring and produces an expected increase in certain common physiologic parameters, such as heart rate and blood pressure. If the patient is not in physical therapy, then location-specific alarm rules may be assigned regarding enunciation of only local alarms at step 130a and the use of elevated alarm limits at step 130b, which is in consideration of the fact that the patient is moving.

This written description uses examples to disclose the invention, including the best mode, and also to enable any person skilled in the art to make and use the invention. Certain terms have been used for brevity, clarity and understanding. No unnecessary limitations are to be inferred therefrom beyond the requirement of the prior art because such terms are used for descriptive purposes only and are intended to be broadly construed. The patentable scope of the invention is defined by the claims, and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

We claim:

1. A patient monitoring system comprising:
   a sensing device configured to measure physiologic parameter data from a patient;
   an identification transmitter that transmits an identification signal, wherein the identification signal is associated with the patient;
   a location tracking system having a plurality of identification receivers arranged in a care facility that receive the identification signal from the identification transmitter, wherein the location tracking system determines a patient location within the care facility based on a location of receipt of the identification signal;
   wherein the plurality of identification receivers includes one primary identification receiver located at a primary location for the patient such that the location tracking system determines that the patient location is the primary location when the identification signal is received by the primary identification receiver;
   a contextual alarming module executable to:
     receive the patient location;
     select at least one location-specific alarm rule based on whether the patient location is the primary location in the care facility; and
     wherein the physiologic parameter data is assessed based on the location-specific alarm rule.

2. The system of claim 1, wherein the location-specific alarm rule includes an alarm modality.

3. The system of claim 1, wherein the location-specific alarm rule includes an alarm generation location in the care facility based on the patient location.

4. The system of claim 1, wherein the location-specific alarm rule requires inclusion of a patient location indicator in an alarm notification.

5. The system of claim 1, wherein the location-specific alarm rule includes an alarm limit based on the patient location for at least one physiologic parameter being measured by the sensing device.

6. The system of claim 1, further comprising an activity sensor attached to the patient and an activity analysis module that determines at least one of a motion indicator or a position indicator based on measurements by the activity sensor, wherein the contextual alarming module further receives the motion indicator and/or position indicator of the patient and determines the location-specific alarm rule based on the motion indicator and/or position indicator of the patient.

7. The system of claim 6, wherein each of the plurality of identification receivers are at a known location in the care facility, and wherein the patient location is determined based on a one of the plurality of identification receivers that receives the identification signal from the identification transmitter.

8. The system of claim 7, wherein sensing device is a wireless sensing device worn on the patient, and the identification transmitter is incorporated into the wireless sensing device.

9. The system of claim 8, wherein the primary identification receiver is in a charger associated with the wireless sensing device.

10. The system of claim 7, wherein the location-specific alarm rule suppresses audio alarm modality when the patient location is at one of a predefined set of patient locations.

11. The system of claim 6, wherein the location-specific alarm rule increases alarm limits when the motion indicator indicates that the patient is moving, the position indicator indicates that the patient is upright, and the patient location is not the primary location for the patient in the care facility.

12. The system of claim 1, wherein the location-specific alarm rule requires inclusion of a patient location indicator in an alarm notification when the patient location is not the primary location for the patient in the care facility.

13. A method of monitoring a patient, the method comprising:
   transmitting an identification signal associated with the patient from an identification transmitter;
   receiving the identification signal at an identification receiver;
   determining whether the identification receiver is a primary identification receiver for the patient, wherein the primary identification receiver is located at a primary location for the patient within a care facility
   determining whether a patient location is at the primary location for the patient within the care facility based on whether the identification receiver receiving the identification signal is the primary identification receiver;
   selecting at least one location-specific alarm rule based on whether the patient location is at the primary location for the patient within the care facility;
   measuring physiologic parameter data from the patient; and
   assessing the physiologic parameter data based on the location-specific alarm rule.

14. The method of claim 13, wherein the location-specific alarm rule includes at least one of an alarm modality and an alarm generation location in the care facility based on the patient location.

15. The method of claim 13, wherein the method further includes selecting a location-specific alarm rule requiring inclusion of a patient location indicator in an alarm notification when the patient location is not the primary location for the patient in the care facility.

16. The method of claim 13, wherein the location-specific alarm rule includes an alarm limit based on the patient location for at least one physiologic parameter being measured on the patient.

17. The method of claim 13, further comprising:
   determining at least one of a motion indicator or a position indicator for the patient; and
   determining the location-specific alarm rule based further on the motion indicator and/or position indicator of the patient.

18. The method of claim 17, wherein the location-specific alarm rule increases alarm limits when the motion indicator indicates that the patient is moving and the position indicator indicates that the patient is upright, and the patient location is not the primary location for the patient in the care facility.

19. The method of claim 13, wherein the primary identification receiver is positioned such that receipt of the identification signal at the primary identification receiver indicates that the patient is in an assigned room for that patient.

20. The method of claim 19, wherein the primary identification receiver is in a charger associated with a wireless sensing device.

* * * * *